(12) United States Patent
Hansen et al.

(10) Patent No.: US 11,591,594 B2
(45) Date of Patent: Feb. 28, 2023

(54) LNA-G PROCESS

(71) Applicant: Roche Innovation Center Copenhagen A/S, Hørsholm (DK)

(72) Inventors: Dennis Jul Hansen, Hørsholm (DK); Joerg Hoernschemeyer, Basel (CH); Jacob Ravn, Hørsholm (DK); Christoph Rosenbohm, Hørsholm (DK)

(73) Assignee: Roche Innovation Center Copenhagen A/S, Basel (CH)

( * ) Notice: Subject to any disclaimer, the term of this patent is extended or adjusted under 35 U.S.C. 154(b) by 0 days.

(21) Appl. No.: 16/812,233

(22) Filed: Mar. 6, 2020

(65) Prior Publication Data

US 2020/0318109 A1 Oct. 8, 2020

Related U.S. Application Data

(63) Continuation of application No. 15/771,223, filed as application No. PCT/EP2016/069765 on Aug. 22, 2016, now abandoned.

(30) Foreign Application Priority Data

Aug. 24, 2015 (EP) .................................... 15182172

(51) Int. Cl.
*C12N 15/11* (2006.01)
*C07H 21/00* (2006.01)
(Continued)

(52) U.S. Cl.
CPC .............. *C12N 15/111* (2013.01); *C07H 1/00* (2013.01); *C07H 21/00* (2013.01); *C12N 15/113* (2013.01);
(Continued)

(58) Field of Classification Search
CPC ........ C07H 21/00; C07H 1/00; C12N 15/111; C12N 15/113; C12N 2310/3231;
(Continued)

(56) References Cited

U.S. PATENT DOCUMENTS 6,998,484 B2 * 2/2006 Koch ..................... C07H 19/04
544/229
2019/0055550 A1 2/2019 Hansen

FOREIGN PATENT DOCUMENTS

JP 2004-536125 12/2004
WO WO98/039352 9/1998
(Continued)

OTHER PUBLICATIONS

"5'-MMT-Amino-Modifiers" technical bulletin published by Glen Research, last updated Jul. 2009, online at https://www.glenresearch.com/media/folio3/productattachments/technical_bulletin/TB_MMT_Amino_Modifiers.pdf (Year: 2009).*
(Continued)

*Primary Examiner* — Eric Olson
(74) *Attorney, Agent, or Firm* — Smith Gambrell & Russell LLP; Judy Jarecki-Black; Noah Wilson

(57) ABSTRACT

Recent advancements in LNA oligonucleotides include the use of amine linkers to link an LNA antisense oligonucleotide to a conjugate group. For example please see WO2014/118267. The present invention originates from the identification of a problem when de-protecting LNA oligonucleotides which comprise an aliphatic amine group and DMF protected LNA G nucleoside, which results in the production of a +28 Da impurity. This problem is solved by using acyl protection groups on the exocyclic nitrogen of the LNA-G residue, rather than the standard DMF protection group.

21 Claims, 8 Drawing Sheets

Figure 1:
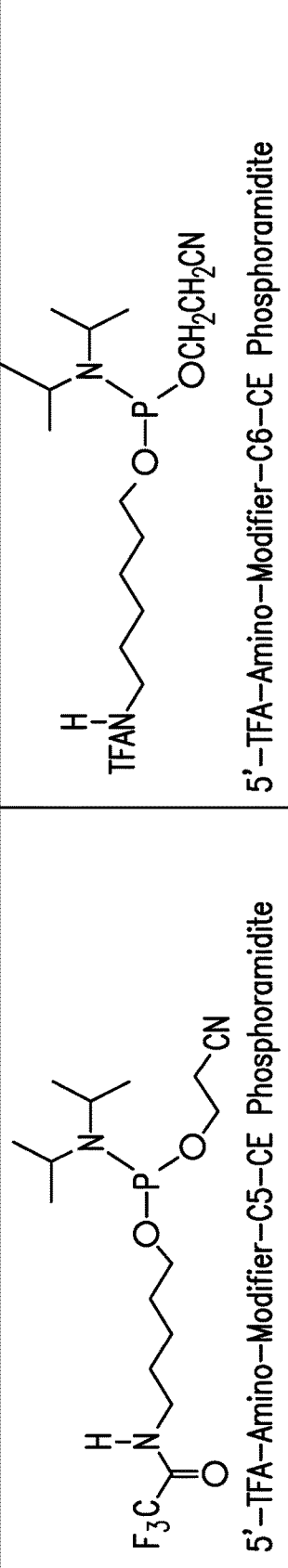
Figure 1:
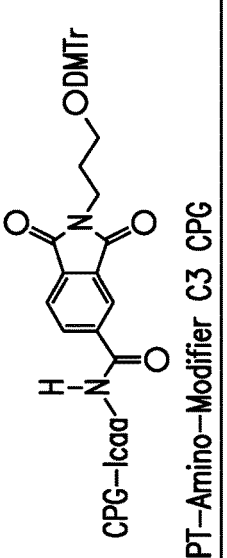
Figure 1:
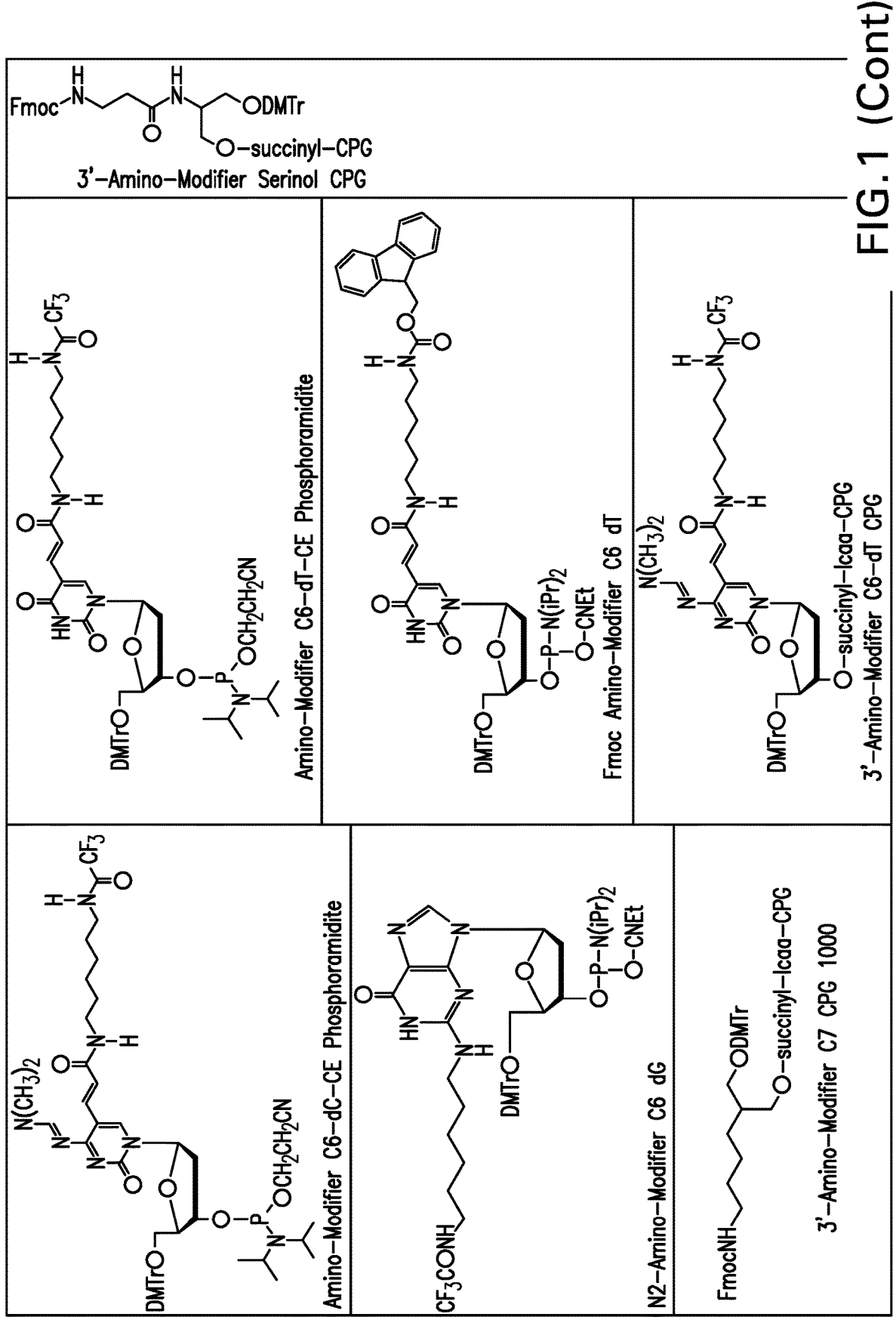

Specification includes a Sequence Listing.

(51) Int. Cl.
*C07H 1/00* (2006.01)
*C12N 15/113* (2010.01)

(52) U.S. Cl.
CPC .............. *C12N 2310/311* (2013.01); *C12N 2310/312* (2013.01); *C12N 2310/314* (2013.01); *C12N 2310/321* (2013.01); *C12N 2310/3231* (2013.01); *C12N 2310/336* (2013.01); *C12N 2310/351* (2013.01); *C12N 2310/3515* (2013.01); *C12N 2330/30* (2013.01)

(58) Field of Classification Search
CPC ........ C12N 2310/336; C12N 2310/351; C12N 2310/321; C12N 2310/314; C12N 2310/312; C12N 2310/311; C12N 2330/30
See application file for complete search history.

(56) References Cited

FOREIGN PATENT DOCUMENTS

| WO | WO99/014226 | 3/1999 |
|---|---|---|
| WO | WO00/047599 | 8/2000 |
| WO | WO00/66604 | 11/2000 |
| WO | WO03/006475 | 1/2003 |
| WO | WO2004/046160 | 6/2004 |
| WO | WO2007/090071 | 8/2007 |
| WO | WO2007/112754 | 10/2007 |
| WO | WO2007/134181 | 11/2007 |
| WO | WO2008/150729 | 12/2008 |
| WO | WO2008/154401 | 12/2008 |
| WO | WO2009/006478 | 1/2009 |
| WO | WO2009/043353 | 4/2009 |
| WO | WO2009/067647 | 5/2009 |
| WO | WO2009/124238 | 10/2009 |
| WO | WO2010/036698 | 4/2010 |
| WO | WO2010/077578 | 7/2010 |
| WO | WO2011/156202 | 12/2011 |
| WO | WO2013/036868 | 3/2013 |
| WO | WO2014/076195 | 5/2014 |
| WO | WO2014/076196 | 5/2014 |
| WO | WO2014/118267 | 8/2014 |
| WO | WO2014/179620 | 11/2014 |

OTHER PUBLICATIONS

Astakhova et al., "LNA for Optimization of Fluorescent Oligonucleotide Probes: Improved Spectral Properties and Target Binding" Bioconjugate Chemistry vol. 22 pp. 533-539 dx.doi.org/10.1021/bc1005027 (Year: 2011).*

Albaek et al., "Analogues of a Locked Nucleic Acid with Three-Carbon 2',4'-Linkages: Synthesis by Ring-Closing Metathesis and Influence on Nucleic Acid Duplex Stability and Structure," J Org Chem., Sep. 8, 2006, 71(20):7731-7740.

Bergstrom, "Unnatural Nucleosides with Unusual Base Pairing Properties," Curr Protoc Nucleic Acid Chem, Jun. 2009, 37:1.4.1-1.

Hirao et al., "Natural versus artificial creation of base pairs in DNA: origin of nucleobases from the perspectives of unnatural base pair studies," Acc Chem Res, Dec. 2012, 45(12):2055-2065.

International Search Report and Written Opinion in International Application No. PCT/EP2016/069765, dated Nov. 11, 2016, 12 pages.

International Preliminary Report on Patentability in International Application No. PCT/EP2016/069765, dated Feb. 27, 2018, 7 pages.

Koshkin et al., "A simplified and efficient route to 2'-0, 4'-C-methylene-linked bicyclic ribonucleosides (Locked Nucleic Acid)", J Org Chem., Dec. 1, 2001, 66(25):8504-8512.

Koshkin et al, "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, Apr. 1998, 54(14):3607-3630.

McLuckey et al, "Decompositions of multiply charged oligonucleotide anions," J Am Chem Soc, Dec. 1993, 115(25):12085-12095.

Mitsuoka et al., "A bridged nucleic acid, 2',4'-BNA COC: synthesis of fully modified oligonucleotides bearing thymine, 5-methylcytosine, adenine and guanine 2',4'-BNA COC monomers and RNA-selective nucleic-acid recognition," Nucleic Acids Res, Mar. 2009, 37(4):1225-1238.

Morita et al., "2'-O,4'-C-ethylene-bridged nucleic acids (ENA): highly nuclease-resistant and thermodynamically stable oligonucleotides for antisense drug," Bioorg Med Chem Lett, Jan. 2002, 12(1):73-76.

Rublack et al., "Synthesis of specifically modified oligonucleotides for application in structural and functional analysis of RNA", J Nucleic Acids, 2011, 24(16):1-19.

Seth at al., "Synthesis and biophysical evaluation of 2',4'-constrained 2'O-methoxyethyl and 2',4'-constrained 2'O-ethyl nucleic acid analogues," J Org Chem, Mar. 2010, 5(5):1569-1581.

Amarnath, V., et al., "Chemical Synthesis of Oligonucleotides", Chemical Reviews, 77(2): 183-217 (1977).

Vinayak, R., et al., "Chemical synthesis of RNA using fast oligonucleotide deprotection chemistry", Nucleic Acids Research, 20(6): 1265-1269 (1992).

* cited by examiner

LNA-G PROCESS

CROSS-REFERENCE TO RELATED APPLICATIONS

This application is a Continuation of U.S. application Ser. No. 15/771,223, which is a national stage application, filed on Apr. 27, 2018 under 35 U.S.C. § 371, of International Patent Application No. PCT/EP2016/069765 filed on Aug. 22, 2016, which claims benefit of and priority to European Patent Application No. 15182172.5 filed on Oct. 24, 2015, all of which are incorporated by reference in their entireties where permissible.

FIELD OF THE INVENTION

The present invention relates to the field of LNA antisense oligonucleotide conjugates and to methods of synthesis thereof.

BACKGROUND TO THE INVENTION

Recent advancements in LNA oligonucleotides include the use of amine linkers to link an LNA antisense oligonucleotide to a conjugate group. For example please see WO2014/118267. The present invention originates from the identification of a problem when de-protecting LNA oligonucleotides which comprise an aliphatic amine group and DMF protected LNA G nucleoside, which results in the production of a +28 Da impurity. This problem is solved by using acyl protection groups on the exocyclic nitrogen of the LNA-G residue, rather than the standard DMF protection group.

STATEMENT OF INVENTION

The invention provides for a method of preparing a LNA oligonucleotide comprising the steps of:
a) Incorporating at least one LNA-G monomer comprising an acyl protected exocyclic nitrogen into an oligonucleotide;
b) Incorporating at least one optionally protected aliphatic amine group into the oligonucleotide;
c) deprotecting the acyl protected exocyclic nitrogen of the at least one LNA-G monomer by removal of the acyl protection group;
wherein steps a) and b) can occur in either order.

Suitably, when present, other G monomers, e.g. DNA G-monomers incorporated into the LNA oligonucleotide, they are also acyl protected on their exocyclic nitrogen, for example by a step of incorporating G-monomer, e.g. a DNA G-monomer or a 2'substituted G-monomer (e.g. 2'-O-methoxyethyl G-monomer, or a 2'-methyl G monomer), wherein the G monomer comprises an acyl protected exocyclic nitrogen into an oligonucleotide, e.g. using a acyl protection group as described herein, e.g. as defined by the R group of formula I.

The invention provides for a method of preparing an LNA oligonucleotide which is essentially free from a +28 adduct comprising the steps of:
a) Incorporating at least one LNA-G monomer comprising an acyl protected exocyclic nitrogen into an oligonucleotide;
b) Incorporating at least one optionally protected aliphatic amine group into the oligonucleotide;
c) deprotecting the acyl protected exocyclic nitrogen of the at least one LNA-G monomer by removal of the acyl protection group;
wherein steps a) and b) can occur in either order.

The invention provides for a method of preparing an LNA oligonucleotide comprising the steps of:
a) Incorporating at least one G monomer comprising an acyl protected exocyclic nitrogen into an oligonucleotide;
b) Incorporating at least one optionally protected aliphatic amine group into the oligonucleotide;
c) deprotecting the acyl protected exocyclic nitrogen of the at least one G monomer by removal of the acyl protection group;
wherein steps a) and b) can occur in either order.

The invention provides for a LNA oligonucleotide which comprises at least one LNA-G monomer comprising an acyl protected exocyclic nitrogen and at least one optionally protected aliphatic amine group, wherein said LNA oligonucleotide is attached to a solid support.

The invention provides for a LNA oligonucleotide which comprises at least one G monomer comprising an acyl protected exocyclic nitrogen and at least one optionally protected aliphatic amine group, wherein said LNA oligonucleotide is attached to a solid support.

The invention provides for an LNA oligonucleotide which comprises at least one LNA-G monomer and at least one optionally protected aliphatic amine group, wherein said LNA oligonucleotide, wherein said oligonucleotide is essentially free of +28 adduct.

The invention provides for an LNA oligonucleotide which comprises at least one G monomer and at least one optionally protected aliphatic amine group, wherein said LNA oligonucleotide, wherein said oligonucleotide is essentially free of +28 adduct.

The invention provides for a pharmaceutical composition comprising an LNA oligomer conjugate which comprises an LNA-G monomer and an aliphatic amine linker positioned between the 5' nucleotide of LNA oligomer and a conjugate moiety, and a pharmaceutically acceptable diluent, carrier or adjuvant, wherein said composition is essentially free of +28 adduct.

The invention provides for a pharmaceutical composition comprising an LNA oligomer conjugate which comprises an G monomer and an aliphatic amine linker positioned between the 5' nucleotide of LNA oligomer and a conjugate moiety, and a pharmaceutically acceptable diluent, carrier or adjuvant, wherein said composition is essentially free of +28 adduct.

The invention provides for the use of an LNA-G monomer comprising an acyl protected exocyclic nitrogen for use in the synthesis of an aliphatic amine containing LNA oligonucleotide.

The invention provides for the use of an LNA-G monomer comprising an acyl protected exocyclic nitrogen for use in the synthesis of an aliphatic amine containing LNA oligonucleotide conjugate.

In some embodiments the LNA-G monomer is a monomer of formula I:

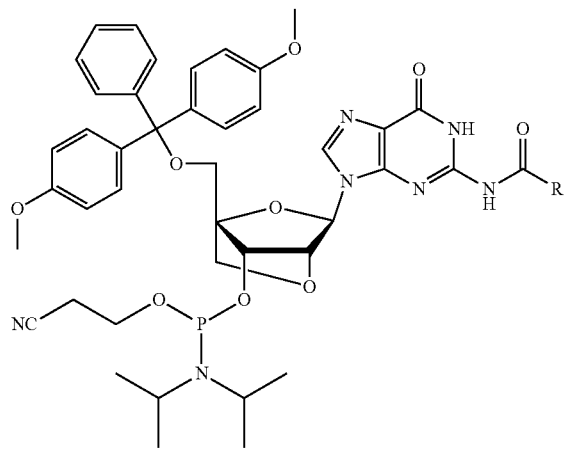

I wherein R may be selected from an optionally substituted alkyl-, alkenyl-, alkynyl-, cycloalkyl- or aryl-group, preferably from an optionally substituted $C_{1-6}$-alkyl-, $C_{2-6}$-alkenyl-, $C_{2-6}$-alkinyl-, $C_{3-7}$-cycloalkyl- or phenyl-group.

If substituted, the R group may be mono or poly substituted, for example with one or more substituents selected from the group consisting of halogen, $C_{1-6}$-alkyl, $C_{2-6}$-alkenyl, $C_{2-6}$-alkynyl, $C_{1-6}$-alkoxy, optionally substituted aryloxy or optionally substituted aryl. Aryl includes phenyl and the optional substituents for aryl are as above.

FIGURES

FIG. 1: Examples of commercially available amino-linkers comprising an aliphatic amine group.

Figure 2:
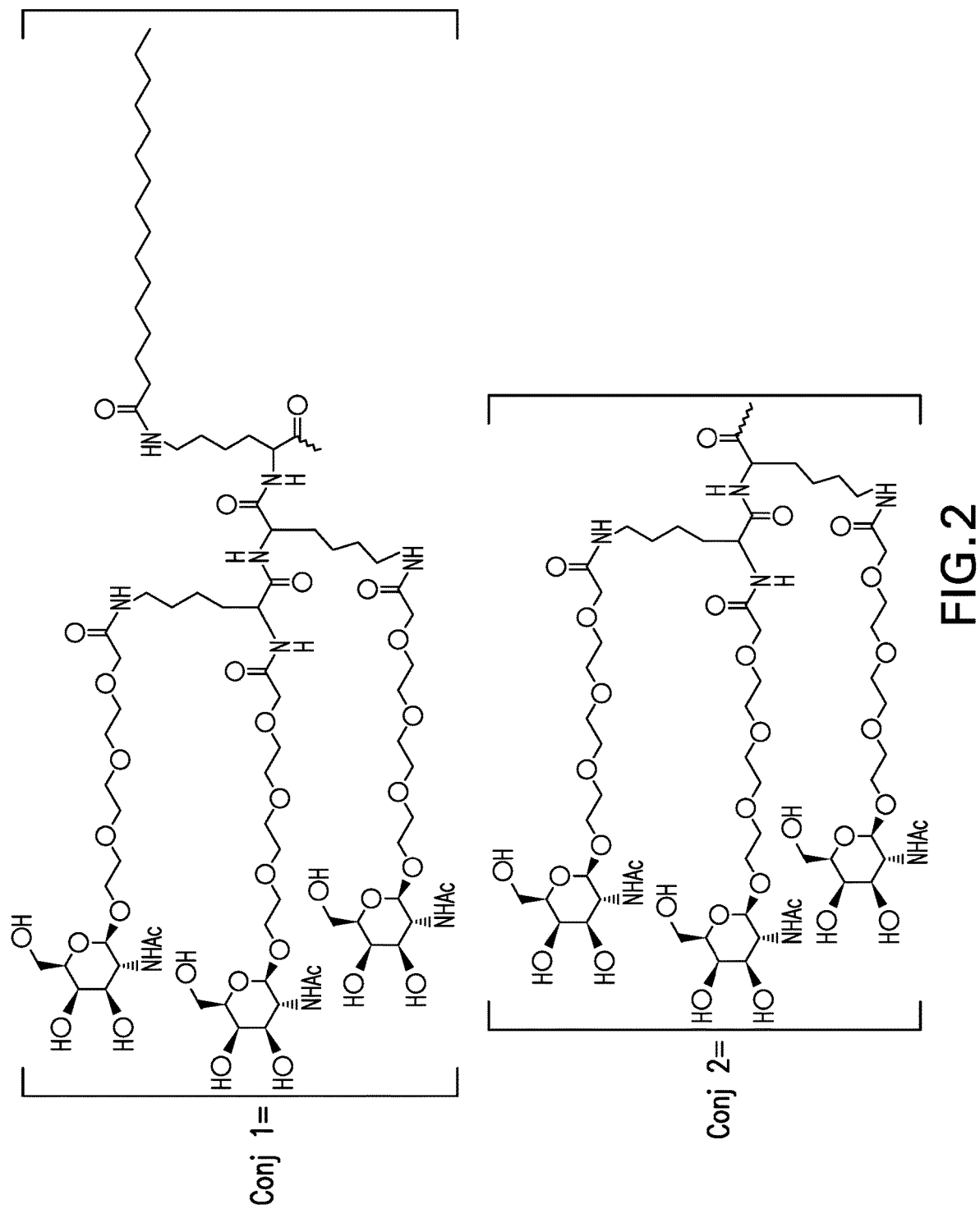

FIG. 2: Examples of GalNAc conjugates.

Figure 3:
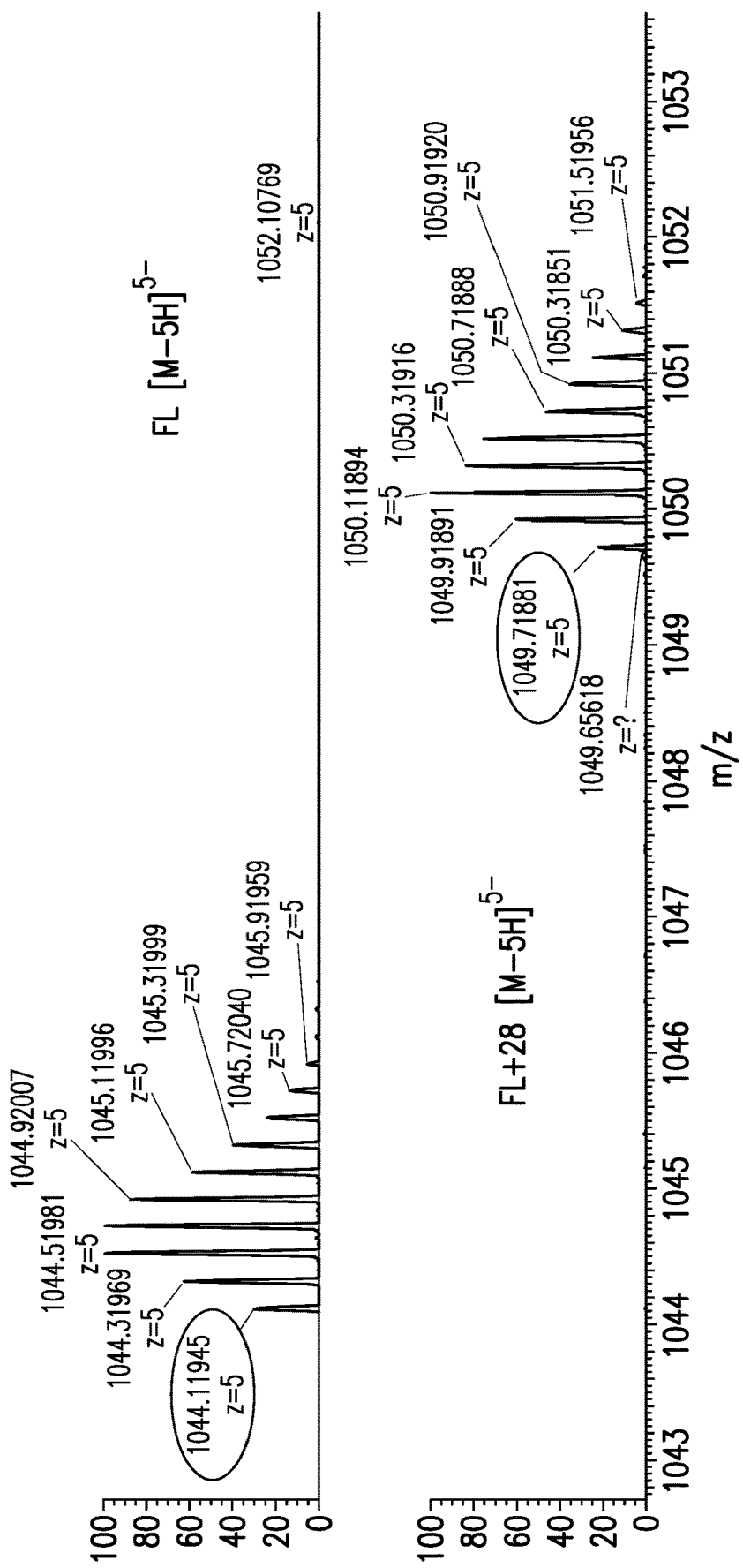

FIG. 3: Mass spectra of FL and FL+28 (five-fold charged ion displayed).

Figure 4:
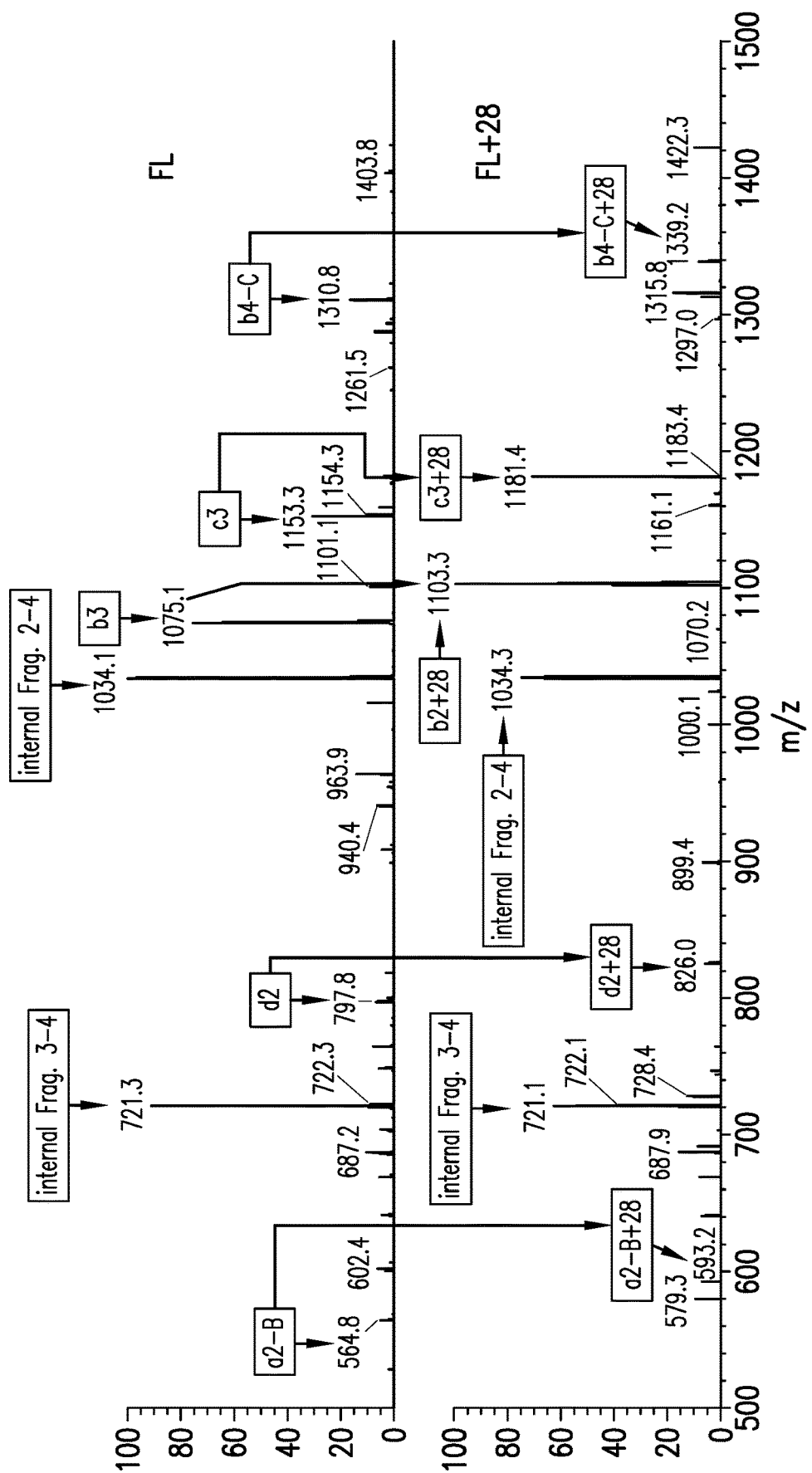

FIG. 4: MS/MS (MS2MS3 fragmentation pattern (excerpt mass range 500-1500 Da) of b4 ions. Peaks with mass difference +28 Da and corresponding peaks in the unmodified molecule are indicated.

Figure 5:
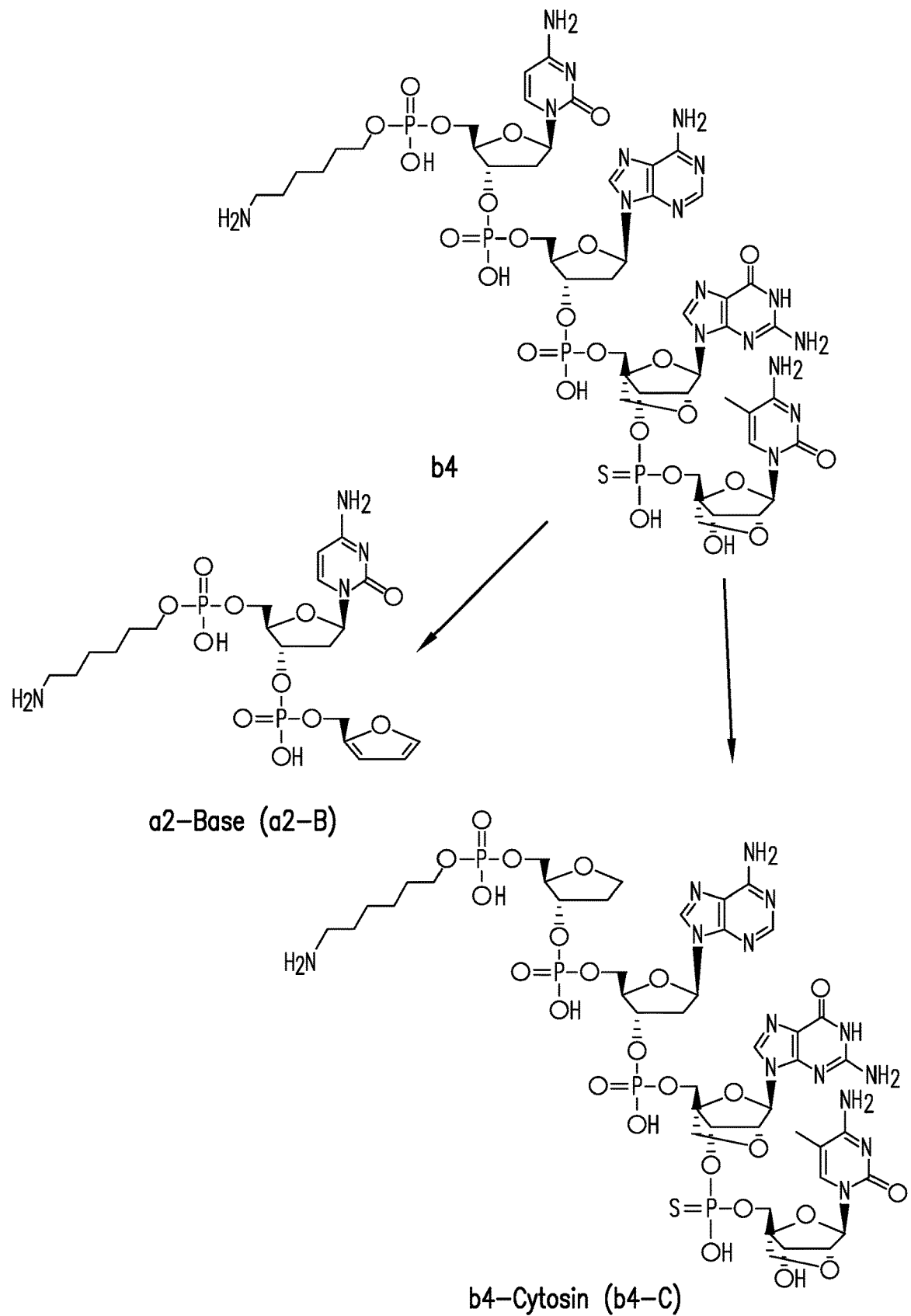

FIG. 5: Structure of the b4-fragment and the resulting a2-Base (a2-B) and the b4-Cytosine (b4-C) fragment from MS3 experiment.

Figure 6:
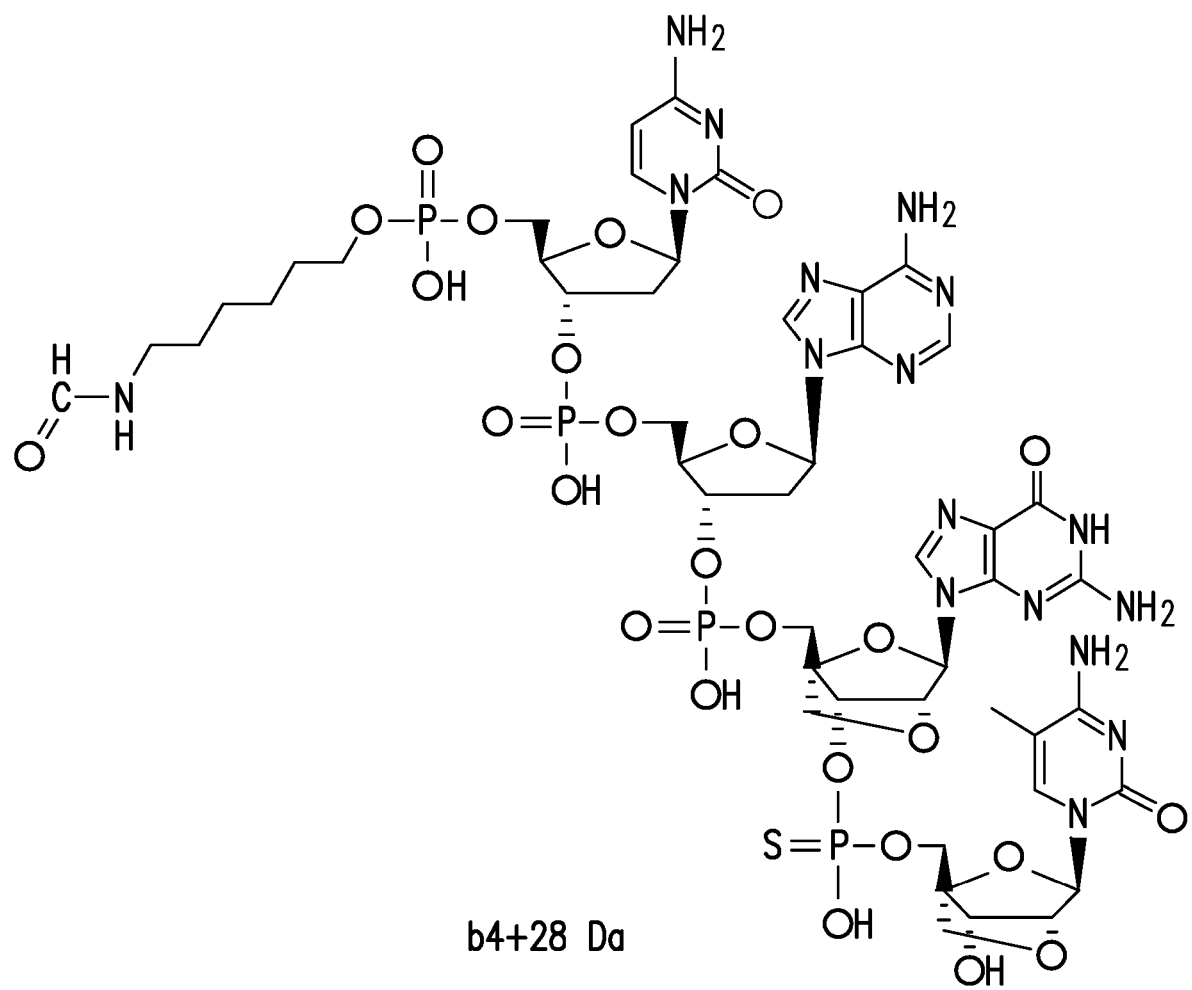

FIG. 6: Structure of the b4-fragment with a formyl amide formed at the C6-amino-linker.

DETAILED DESCRIPTION

The invention provides a method of preparing an oligonucleotide which comprises at least one LNA-G nucleoside and an aliphatic amine group. It has been found by the present inventors that a +28 Da adduct (referred to as the +28 adduct herein) is formed when deprotecting DMF protected LNA-G in the presence of an aliphatic amine. The formation of the +28 adduct may be avoided by using an acyl protection group. The presence of +28 adduct may be identified using mass spectroscopy, by a contaminant in the oligonucleotide with +28 molecular weight. As is illustrated in the example the +28 adduct may be measured using mass spectroscopy, and may have a MW of about +28, for example the +28 adduct may have a MW of +27.5-+28.5 (Da), such as +27.9-+28.1 (Da). This impurity is difficult to separate from the desired oligonucleotide product, and requires additional down-stream purification steps, increasing the cost of production and dramatically reducing the oligonucleotide yield. It is therefore highly desirable to avoid the production of the +28 adduct, and it has been found by the present inventors that this may be achieved by using G-protection groups other than DMF, in particular an acyl or carbamate protection group.

An LNA oligonucleotide is an oligonucleotide which comprises at least one LNA nucleoside. The invention therefore relates to methods of preparing LNA antisense oligonucleotides which comprise at least one LNA-G monomer and at least one aliphatic amine group. The LNA oligonucleotide may be an antisense oligonucleotide. The term oligonucleotide as used herein is defined as it is generally understood by the skilled person as a molecule comprising two or more covalently linked nucleosides. For use as an antisense oligonucleotide, oligonucleotides are typically synthesised as 7-30 nucleotides in length.

The term "antisense oligonucleotide" as used herein is refers to oligonucleotides capable of modulating expression of a target gene by hybridizing to a target nucleic acid, in particular to a contiguous sequence on a target nucleic acid. An antisense oligonucleotide can also be defined by it's complementary to a target nucleic acid. Antisense oligonucleotides are single stranded. Antisense oligonucleotides are not essentially double stranded and are not therefore siRNAs. An antisense oligonucleotide comprises a contiguous oligonucleotide which is complementary to a target nucleic acid. Antisense oligonucleotides typically comprise one or more modified internucleoside linkages, and may by way of a non-limiting example be in the form of an LNA gapmer or a mixed wing gapmer. In other embodiments the oligonucleotide may be an LNA mixmers (LNA and non-LNA nucleotides, e.g. LNA and DNA (see e.g. WO2007/112754 hereby incorporated by reference), or LNA and 2'-O-MOE nucleotides, or LNA, DNA and 2'O-MOE nucleotides), or a LNA totalmers (only LNA nucleotides—see. E.g. WO2009/043353 hereby incorporated by reference).

The term "modified internucleoside linkage" is defined as generally understood by the skilled person as linkages other than phosphodiester (PO) linkages, that covalently couples two nucleosides together. Modified internucleoside linkages are particularly useful in stabilizing oligonucleotides for in vivo use, and may serve to protect against nuclease cleavage. A phosphorothioate internucleoside linkage is particularly useful due to nuclease resistance, beneficial pharmakokinetics and ease of manufacture. In some embodiments at least 70%, such as at least 80% or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate. Further internucleoside linkers are disclosed in WO2009/124238 (incorporated herein by reference).

The term "essentially free" is defined by the level of +28 adduct is less than 5%, such as less than 1%, such as less than 0.5%, such as less than 0.1%, of the oligonucleotide composition prepared by the methods of the invention. An oligonucleotide which is "essentially free" of the +28 adduct may therefore comprise a small amount of +28 adduct, and in some embodiments the level of +28 adduct may be below the level of detection using mass spectroscopy. In term essentially free comprises the embodiment where the oligonucleotide product is free of +28 adduct.

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In some embodiments the nucleobase moiety is modified by modifying or replacing the nucleobase. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Modified nucleosides and nucleotides are modified as compared to the equivalent DNA or RNA nucleoside/tide by the introduction of a modification to the ribose sugar moiety, the nucleobase moiety, or in the case of modified nucleotides, the internucleoside linkage. Nucleosides and nucleotides may also interchangeably be referred to as "units" or "monomers".

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. The term modified nucleoside may also be used herein interchangeably with the term "nucleoside analogue" or modified "units" or modified "monomers". Examples of modified nucleosides are described in the separate section "Oligomer modifications" and its sub-sections.

Acyl Protected Exocyclic Nitrogen

The exocyclic nitrogen group of guanine is illustrated below (encircled). This group is protected by an acyl group during steps a) and b) of the method of the invention, and is removed during the deprotection step c).

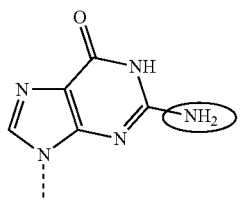

The Aliphatic Amine Group

An aliphatic amine is an amine where there are no aromatic rings directly on the nitrogen atom, and is therefore typically a non nucleosidic amine group. A nucleosidic amine group is an amine group where the nitrogen atom of the amine is directly bound to the aromatic ring of a purine or pyrimidine base.

The aliphatic amine group may be a primary amine or a secondary amine.

In some embodiments, the aliphatic amine group is selected from the group consisting of an amino alkyl, alkylamino alkyl, piperidinyl, piperazinyl, pyrrolidinyl, and imidazolyl.

In some embodiments, the aliphatic amine group is selected from the group consisting of 5'-TFA-Amino-Modifier-C5-CE Phosphoramidite, 5'-TFA-Amino-Modifier C6-CE Phosphoramidite, 11-(trifluoroacetamido)-3,6,9-trioxaundecan-1-yl-[(2-cyanoethyl)-(N,N-diisopropyl)]-phosphoramidite, 5'-TFA-Amino-Modifier-C12-CE Phosphoramidite, Amino-Modifier C2-dT-CE Phosphoramidite, Amino-Modifier C6-dA-CE Phosphoramidite, Amino-Modifier C6-dA-CE Phosphoramidite, Amino-Modifier C6-dT-CE Phosphoramidite, $N^2$-Amino-Modifier C6 dG, Fmoc Amino-Modifier C6 dT, 3'-Amino-Modifier C7 CPG 1000, 3'-Amino-Modifier C6-dC CPG, 3'-Amino-Modifier C6-dC CPG, 3'-PT-Amino-Modifier C6 CPG, 3'-Amino-Modifier C6-dT CPG, PC 5'-Amino-Modifier-CE Phosphoramidite, 5'-Amino-Modifier C6-PDA, 5'-Amino-Modifier C12-PDA, 5'-Amino-Modifier TEG PDA, Amino-Modifier Serinol, 3'-Amino-Modifier Serinol CPG In some embodiments, the aliphatic amine group is in the form of an amino linker (i.e. the amino linker comprises the aliphatic amine group). Examples of commercially available amino linkers are shown in FIG. 1. In some embodiments, the amino linker is an aminoalkyl linker, such as a $C_{2-12}$ aminoalkyl linker, for example an amino hexyl linker.

In some embodiments the aliphatic amino group is protected, for example with a protection group selected from the list comprising of trifluoroacetyl (TFA), trichloroacetyl (TCA), monomethoxytrityl (MMT), dimethoxytrityl (DMT), fluorenylmethyloxycarbonyl (Fmoc), phtalimide or 2-(methylaminocarbonyl)-benzoate. In some embodiments the amine protection group, when present, is removed prior to or during the deprotection step c).

It is recognised that some aliphatic amine protection groups may survive step c), and as such they provide an alternative method of avoiding the +28 adduct. The invention therefore provides an alternative method of preparing a LNA oligonucleotide comprising the steps of:

a) incorporating at least one protected exocyclic nitrogen LNA-G monomer into an oligonucleotide b) incorporating at least one protected aliphatic amine group into the oligonucleotide c) deprotecting the at least one exocyclic nitrogen LNA-G monomer containing oligonucleotide by removal of the exocyclic nitrogen protection group d) subsequent to step c), deprotecting the aliphatic amine group.

The deprotection step c) may comprise exposure of the oligonucleotide to ammonium hydroxide, and suitably the aliphatic amine protection group are not cleaved under the deprotection conditions of step c) (i.e. by ammonium hydroxide treatment). In the above method the exocyclic nitrogen protection group may be an acyl group or may be another protection group such as dimethylformamide (DMF). The aliphatic amine protection group may, for example, be selected from the group consisting of TFA, monomethoxytrityl (MMT), DMT, Fmoc, phtalimide or 2-(methylaminocarbonyl)-benzoate In some embodiments, the aliphatic amine group, such as the amino linker, is attached to a solid support used for oligonucleotide synthesis. The cleavage of the oligonucleotide from the solid support (which may be during step c)) will therefore result in the cleavage of the aliphatic amine group from the solid support and thereby release of the oligonucleotide from the solid support. In some embodiments, the aliphatic amine group is incorporated into the oligonucleotide via the incorporation of an amino-modified monomer. In some embodiments, the aliphatic amino-modified monomer is a phosphoramidite, a H-phosphonate or a phosphotriester monomer. In some embodiments, the amino-modified monomer is a phosphoramidite. Examples of such amino-modified monomers are shown in FIG. 1.

The aliphatic amine group may be incorporated into the oligonucleotide via any suitable oligonucleotide synthesis method, such as H-phosphonate synthesis, phosphodiester synthesis, phosphotriester synthesis, phosphite trimester synthesis or phosphoramidite oligonucleotide synthesis. In some embodiments the aliphatic amine group is incorporated into the oligonucleotide as phosphoramidite, a H-phosphonate or a phosphotriester. In some embodiments the aliphatic amine group is incorporated into the oligonucleotide during phosphoramidite oligonucleotide synthesis.

The Acyl Protection Group

The use of an acyl protection group on the exocyclic nitrogen of G residues allows for the avoidance of the +28 adduct in methods of synthesis of aliphatic amine containing oligonucleotides.

Some non-limiting examples of suitable acyl protection groups on the exocyclic nitrogen of the LNA-G monomer(s) may be selected from the group consisting of isobutyryl (iBu), acetyl (Ac), phenoxyacetyl (PAC), p-isopropylphenoxyacetyl (iPrPAC), phenylacetyl, Isopropyloxyacetyl, methoxyacetyl, benzoyl, p-methoxyphenylacetyl, diphenylacetyl, cyclohexylcarbonyl, 1,1-dimethylpropanoyl, and p-tert-Butyl-phenoxyacetyl.

In some embodiments, the acyl protection group on the exocyclic nitrogen of the LNA-G monomer(s) is selected from the group consisting of isobutyryl (iBu), acetyl (Ac), phenoxyacetyl (PAC), and p-isopropylphenoxyacetyl (iPrPAC).

In an alternative embodiment, the acyl protection group may be replaced with a carbamate protection group.

The LNA G Monomer

The term LNA-G refers to a nucleoside which comprises a 2'-4' biradical in the furanose ring and a guanine nucleobase. The LNA-G monomer may be incorporated into the oligonucleotide via any suitable oligonucleotide synthesis method, such as H-phosphonate synthesis, phosphodiester synthesis, phosphotriester synthesis, phosphite triester synthesis or phosphoramidite oligonucleotide synthesis. In some embodiments the LNA-G monomer(s) is incorporated into the oligonucleotide as phosphoramidite, a H-phosphonate or a phosphotriester. In some embodiments the LNA-G monomer is incorporated into the oligonucleotide during phosphoramidite oligonucleotide synthesis.

In some embodiments, the LNA oligonucleotide comprises at least 1 G monomers, such as at least 2 G monomers, such as at least 3 G monomers, such as at least 4 G monomers.

Oligonucleotide Synthesis (Step a) and Steps a) and b))

The method of preparing an oligonucleotide may utilise any suitable oligonucleotide synthesis method, such as H-phosphonate synthesis, phosphodiester synthesis, phosphotriester synthesis, phosphite triester synthesis or phosphoramidite oligonucleotide synthesis. The LNA-G monomer and optionally the aliphatic amine group (optionally protected) may in a form which allows for incorporation into the oligonucleotide during such standard oligonucleotide methods (e.g. as a phosphoramidite).

Deprotection Step c)

Step c) of the method of the invention comprises the removal of the acyl protection group from the exocyclic nitrogen in the LNA-G monomer incorporated into the oligonucleotide. Deprotection may further comprise the removal of other base protection groups, and optionally the removal of the aliphatic amine protection group, when present. During solid phase synthesis of oligonucleotides, the deprotection step may further result in the cleavage of the oligonucleotide from the solid support, deprotection (and optionally cleavage) of the oligonucleotide may performed in the presence of ammonia, such as using a solution comprising ammonium hydroxide. For example, concentrated ammonium hydroxide may be used (e.g. (28 to 33% $NH_3$ in water), or a 1:1 mixture of ammonium hydroxide and aqueous methylamine (AMA). Other deprotection methods are known in the art.

Conjugation Step

The oligonucleotides synthesised according to the method of the invention are particularly useful for making oligonucleotide conjugates as the aliphatic amine group provides an amenable conjugation site. Oligonucleotide conjugates comprise an oligonucleotide which is covalently linked to a non-nucleoside moiety, which may for example be a lipid, a sterol, a carbohydrate, a peptide and a protein. Examples of conjugate moieties are disclosed in WO2014/076195 and WO2014/179620, which are hereby incorporated by reference.

In some embodiments, the method of the invention comprises an additional step performed subsequent to step c) which comprises comprises incorporating a conjugate group onto the aliphatic primary amine group.

The invention therefore provides for a method of preparing a LNA oligonucleotide conjugate comprising the steps of:

a) incorporating at least one nitrogen LNA-G monomer comprising an acyl protected exocyclic nitrogen into an oligonucleotide b) incorporating at least one optionally protected aliphatic amine group into the oligonucleotide c) deprotecting the at least one acyl protected exocyclic nitrogen of the at least one LNA-G monomer oligonucleotide by removal of the acyl protection group.

d) incorporating a conjugate group onto the aliphatic amine group.

wherein steps a) and b) can occur in either order or simultaneously.

In some embodiments the conjugate moiety is a carbohydrate, such as a N-acetylgalactosamine (GalNAc) conjugates, see WO2014/118267, which is hereby incorporated by reference. GalNaC conjugates are useful in enhancing uptake into cells, such as liver cells, and are typically use as a GalNAc cluster, such as a trivalent GalNAc cluster. Examples of GalNAc conjugates which may be incorporated into oligonucleotides using the methods of the invention are illustrated in FIG. 2.

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety to a first region, e.g. an oligonucleotide (region A).

In the context of the present invention the linker may comprise the aliphatic amine group, such as a primary or secondary aliphatic amine group. In some embodiments the linker is an aliphatic amino alkyl, such as a $C_2$-$C_{38}$ aliphatic amino alkyl group, including, for example $C_6$ to $C_{12}$ aliphatic amino alkyl groups. In some embodiments the linker is a $C_6$ aliphatic amino alkyl group. In some embodiments the oligonucleotide comprises a region of DNA phosphodiester nucleotides, e.g. 1-5 DNA PO nucleotides which are positioned between the antisense oligonucleotide and the aliphatic amino linker—see WO2014/076195 hereby incorporated by reference.

Locked Nucleic Acid Nucleosides (LNA).

LNA nucleosides are modified nucleosides which comprise a linker group (referred to as a biradicle or a bridge) between C2' and C4' of the ribose sugar ring of a nucleotide.

These nucleosides are also termed bridged nucleic acid or bicyclic nucleic acid (BNA) in the literature.

In some embodiments, the modified nucleoside or the LNA nucleosides of the oligomer of the invention has a general structure of the formula I or II:

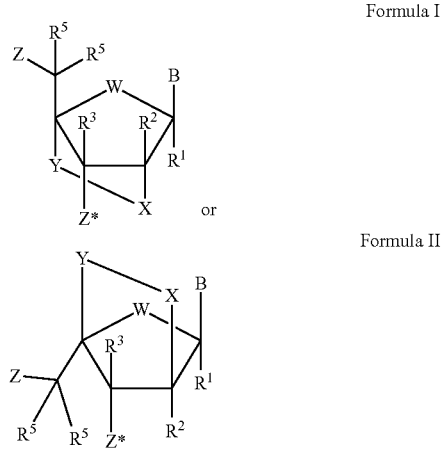

Formula I

Formula II wherein W is selected from —O—, —S—, —N($R^8$)—, —C($R^aR^b$)—, such as, in some embodiments —O—;

B designates a nucleobase or modified nucleobase moiety:

Z designates an internucleoside linkage to an adjacent nucleoside, or a 5'-terminal group;

Z* designates an internucleoside linkage to an adjacent nucleoside, or a 3'-terminal group;

X designates a group selected from the list consisting of —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, X is selected from the group consisting of: —O—, —S—, NH—, N$R^aR^b$, —CH$_2$—, CR$^a$R$^b$, —C(=CH$_2$)—, and —C(=CR$^a$R$^b$)—

In some embodiments, X is —O—

Y designates a group selected from the group consisting of —C($R^aR^b$)—, —C($R^1$)=C($R^b$)—, —C($R^a$)=N—, —O—, —Si($R^a$)$_2$—, —S—, —SO$_2$—, —N($R^a$)—, and >C=Z In some embodiments. Y is selected from the group consisting of: —CH$_2$—, —C($R^aR^b$)—, —CH$_2$CH$_2$—, —C($R^aR^b$)—C($R^aR^b$)—, —CH$_2$CH$_2$CH$_2$—, —C($R^aR^b$)C($R^aR^b$)C($R^aR^b$)—, —C($R^a$)=C($R^b$)—, and —C($R^a$)=N—

In some embodiments, Y is selected from the group consisting of: —CH$_2$—, —CHR$^a$—, —CHCH$^a$—, CR$^a$R$^b$— or —X—Y— together designate a bivalent linker group (also referred to as a radicle) together designate a bivalent linker group consisting of 1, 2, or 3 groups/atoms selected from the group consisting of —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z.

In some embodiments, —X—Y— designates a biradicle selected from the groups consisting of: —X—CH$_2$—, —X—CR$^a$R$^b$—, —X—CHR$^a$—, —X—C(HCH$_3$)—, —O—Y—, —O—CH$_2$—, —S—CH$_2$—, —NH—CH$_2$—, —O—CHCH$_3$—, —CH$_2$O—CH$_2$—, —O—CH(CH$_3$CH$_3$)—, —O—CH$_2$—CH$_2$—, OCH$_2$—CH$_2$—, —O—CH$_2$OCH$_2$—, —O—NCH$_2$—, —C(=CH$_2$)—CH$_2$—, —NR$^8$—CH$_2$—, N—O—CH$_2$, —S—CR$^aR^b$— and —S—CHR$^a$—.

In some embodiments —X—Y— designates —O—CH$_2$— or —O—CH(CH$_3$)—.

wherein Z is selected from —O—, —S—, and —N($R^a$)—, and $R^a$ and, when present $R^b$, each is independently selected from hydrogen, optionally substituted $C^{1-6}$-alkyl, optionally substituted $C_{2-6}$-alkenyl, optionally substituted $C_{2-6}$-alkynyl, hydroxy, optionally substituted $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkyl-thio, halogen, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation.

wherein $R^1$, $R^2$, $R^3$, $R^5$ and $R^{5*}$ are independently selected from the group consisting of: hydrogen, optionally substituted $C_{1-6}$-alkyl, optionally substituted $C_{2-6}$-alkenyl, optionally substituted $C_{2-6}$-alkynyl, hydroxy, $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C^{1-6}$-alkylthio, halogen, where aryl and heteroaryl may be optionally substituted, and where two geminal substituents together may designate oxo, thioxo, imino, or optionally substituted methylene.

In some embodiments $R^1$, $R^2$, $R^3$, $R^5$ and $R^{5*}$ are independently selected from $C_{1-6}$ alkyl, such as methyl, and hydrogen.

In some embodiments $R^1$, $R^2$, $R^3$, $R^5$ and $R^{5*}$ are all hydrogen.

In some embodiments $R^1$, $R^2$, $R^3$, are all hydrogen, and either $R^5$ and $R^{5*}$ is also hydrogen and the other of $R^5$ and $R^{5*}$ is other than hydrogen, such as $C_{1-6}$ alkyl such as methyl.

In some embodiments, $R^a$ is either hydrogen or methyl. In some embodiments, when present, $R^b$ is either hydrogen or methyl.

In some embodiments, one or both of $R^a$ and $R^b$ is hydrogen

In some embodiments, one of $R^a$ and $R^b$ is hydrogen and the other is other than hydrogen In some embodiments, one of $R^a$ and $R^b$ is methyl and the other is hydrogen In some embodiments, both of $R^a$ and $R^b$ are methyl.

In some embodiments, the biradicle —X—Y— is —O—CH$_2$—, W is O, and all of $R^1$, $R^2$, $R^3$, $R^5$ and $R^{5*}$ are all hydrogen. Such LNA nucleosides are disclosed in WO99/014226, WO00/66604, WO98/039352 and WO2004/046160 which are all hereby incorporated by reference, and include what are commonly known as beta-D-oxy LNA and alpha-L-oxy LNA nucleosides.

In some embodiments, the biradicle —X—Y— is —S—CH$_2$—, W is O, and all of $R^1$, $R^2$, $R^3$, $R^5$ and $R^{5*}$ are all hydrogen. Such thio LNA nucleosides are disclosed in WO99/014226 and WO2004/046160 which are hereby incorporated by reference.

In some embodiments, the biradicle —X—Y— is —NH—CH$_2$—, W is O, and all of $R^1$, $R^2$, $R^3$, $R^5$ and $R^{5*}$ are all hydrogen. Such amino LNA nucleosides are disclosed in WO99/014226 and WO2004/046160 which are hereby incorporated by reference.

In some embodiments, the biradicle —X—Y— is —O—CH$_2$—CH$_2$— or —O—CH$_2$—CH$_2$—CH$_2$—, W is O, and all of $R^1$, $R^2$, $R^3$, $R^5$ and $R^{5*}$ are all hydrogen. Such LNA nucleosides are disclosed in WO00/047599 and Morita et al, Bioorganic & Med. Chem. Lett. 12 73-76, which are hereby incorporated by reference, and include what are commonly known as 2'-O-4'C-ethylene bridged nucleic acids (ENA).

In some embodiments, the biradicle —X—Y— is —O—CH$_2$—, W is O, and all of $R^1$, $R^2$, $R^3$, and one of $R^5$ and $R^{5*}$ are hydrogen, and the other of $R^5$ and $R^{5*}$ is other than hydrogen such as $C_{1-6}$ alkyl, such as methyl. Such 5' substituted LNA nucleosides are disclosed in WO2007/134181 which is hereby incorporated by reference.

In some embodiments, the biradicle —X—Y— is —O—CR$^a$R$^b$—, wherein one or both of $R^a$ and $R^b$ are other than hydrogen, such as methyl, W is O, and all of $R^1$, $R^2$, $R^3$, and one of $R^5$ and $R^{5*}$ are hydrogen, and the other of $R^5$ and $R^{5*}$ is other than hydrogen such as $C_{1-6}$ alkyl, such as methyl. Such bis modified LNA nucleosides are disclosed in WO2010/077578 which is hereby incorporated by reference.

In some embodiments, the biradicle —X—Y— designate the bivalent linker group —O—CH(CH$_2$OCH$_3$)— (2'-O-methoxyethyl bicyclic nucleic acid—Seth at al., 2010, J. Org. Chem., 2010, 75 (5), pp 1569-1581). In some embodiments, the biradicle —X—Y— designate the bivalent linker group —O—CH(CH$_2$CH$_3$)— (2'-O-ethyl bicyclic nucleic acid—Seth at al., 2010. J. Org. Chem). In some embodiments, the biradicle —X—Y— is —O—CHR$^a$—, W is O, and all of $R^1$, $R^2$, $R^3$, $R^5$ and $R^{5*}$ are all hydrogen. Such 6' substituted LNA nucleosides are disclosed in WO10036698 and WO07090071 which are both hereby incorporated by reference.

In some embodiments, the biradicle —X—Y— is —O—CH(CH$_2$OCH$_3$)—, W is O, and all of $R^1$, $R^2$, $R^3$, $R^5$ and $R^{5*}$ are all hydrogen. Such LNA nucleosides are also known as cyclic MOEs in the art (cMOE) and are disclosed in WO07090071.

In some embodiments, the biradicle —X—Y— designate the bivalent linker group —O—CH(CH$_3$)—. — in either the R- or S-configuration. In some embodiments, the biradicle —X—Y— together designate the bivalent linker group —O—CH$_2$—O—CH$_2$— (Seth at al., 2010, J. Org. Chem). In some embodiments, the biradicle —X—Y— is —O—CH(CH$_3$)—, W is O, and all of $R^1$, $R^2$, $R^3$, $R^5$ and $R^{5*}$ are all hydrogen. Such 6' methyl LNA nucleosides are also known as cET nucleosides in the art, and may be either (S)cET or (R)cET stereoisomers, as disclosed in WO07090071 (beta-D) and WO2010/036698 (alpha-L) which are both hereby incorporated by reference).

In some embodiments, the biradicle —X—Y— is —O—CR$^a$R$^b$—, wherein in neither R$^a$ or R$^b$ is hydrogen, W is O, and all of $R^1$, $R^2$, $R^3$, $R^5$ and $R^{5*}$ are all hydrogen. In some embodiments, R$^a$ and R$^b$ are both methyl. Such 6' di-substituted LNA nucleosides are disclosed in WO 2009006478 which is hereby incorporated by reference.

In some embodiments, the biradicle —X—Y— is —S—CHR$^a$—, W is O, and all of $R^1$, $R^2$, $R^3$, $R^5$ and $R^{5*}$ are all hydrogen. Such 6' substituted thio LNA nucleosides are disclosed in WO11156202 which is hereby incorporated by reference. In some 6' substituted thio LNA embodiments R$^a$ is methyl.

In some embodiments, the biradicle —X—Y— is —C(=CH2)-C(R$^a$R$^b$)—, such as —C(=CH$_2$)—CH$_2$—, or —C(=CH$_2$)—CH(CH$_3$)—W is O, and all of $R^1$, $R^2$, $R^3$, $R^5$ and $R^{5*}$ are all hydrogen. Such vinyl carbo LNA nucleosides are disclosed in WO08154401 and WO09067647 which are both hereby incorporated by reference.

In some embodiments the biradicle —X—Y— is —N(—OR$^a$)—, W is O, and all of $R^1$, $R^2$, $R^3$, $R^5$ and $R^{5*}$ are all hydrogen. In some embodiments R$^a$ is $C_{1-6}$ alkyl such as methyl. Such LNA nucleosides are also known as N substituted LNAs and are disclosed in WO2008/150729 which is hereby incorporated by reference. In some embodiments, the biradicle —X—Y— together designate the bivalent linker group —O—NR$^a$—CH$_3$— (Seth at al., 2010. J. Org. Chem). In some embodiments the biradicle —X—Y— is —N(R$^a$)—, W is O, and all of $R^1$, $R^2$, $R^3$, $R^5$ and $R^{5*}$ are all hydrogen. In some embodiments R$^a$ is $C_{1-6}$ alkyl such as methyl.

In some embodiments, one or both of $R^5$ and $R^{5*}$ is hydrogen and, when substituted the other of $R^5$ and $R^{5*}$ is $C_{1-6}$ alkyl such as methyl. In such an embodiment, $R^1$, $R^2$, $R^3$, may all be hydrogen, and the biradicle —X—Y— may be selected from —O—CH$_2$— or —O—C(HCR$^a$)—, such as —O—CH(CH$_3$)—.

In some embodiments, the biradicle is —CR$^a$R$^b$—O—CR$^a$R$^b$—, such as CH$_2$—O—CH$_2$—, W is O and all of $R^1$, $R^2$, $R^3$, $R^5$ and $R^{5*}$ are all hydrogen. In some embodiments $R^8$ is $C_{1-6}$ alkyl such as methyl. Such LNA nucleosides are also known as conformationally restricted nucleotides (CRNs) and are disclosed in WO2013036868 which is hereby incorporated by reference.

In some embodiments, the biradicle is —O—CR$^a$R$^b$—O—CR$^a$R$^b$—, such as O—CH$_2$O—CH$_2$—, W is O and all of $R^1$, $R^2$, $R^3$, $R^5$ and $R^{5*}$ are all hydrogen. In some embodiments R$^a$ is $C_{1-6}$ alkyl such as methyl. Such LNA nucleosides are also known as COC nucleotides and are disclosed in Mitsuoka et al., Nucleic Acids Research 2009 37(4), 1225-1238, which is hereby incorporated by reference.

It will be recognized than, unless specified, the LNA nucleosides may be in the beta-D or alpha-L stereoisoform.

Certain examples of LNA nucleosides are presented in Scheme 1.

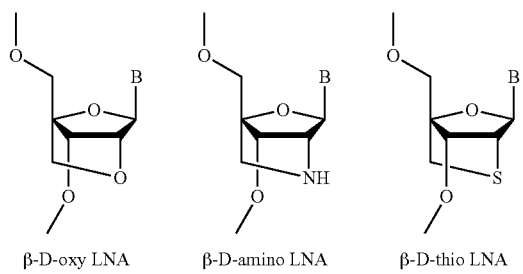

β-D-oxy LNA     β-D-amino LNA     β-D-thio LNA

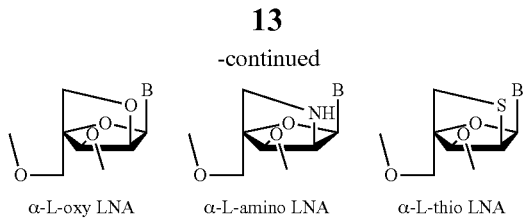

α-L-oxy LNA     α-L-amino LNA     α-L-thio LNA

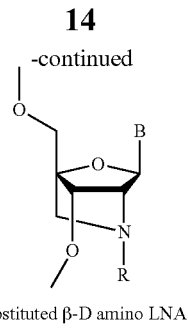

Substituted β-D amino LNA

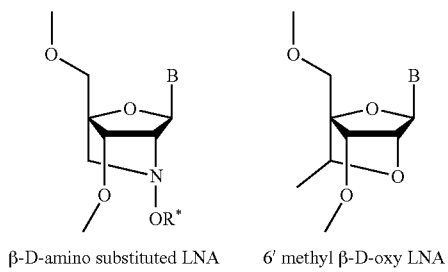

β-D-amino substituted LNA     6' methyl β-D-oxy LNA

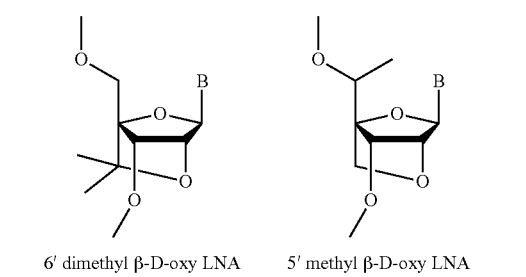

6' dimethyl β-D-oxy LNA     5' methyl β-D-oxy LNA

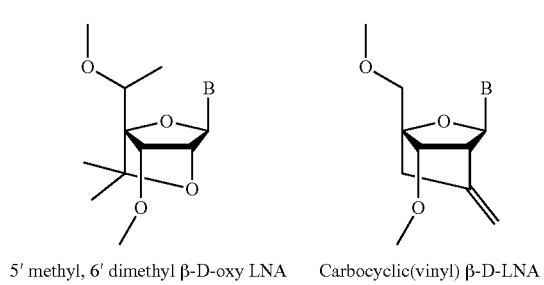

5' methyl, 6' dimethyl β-D-oxy LNA     Carbocyclic(vinyl) β-D-LNA

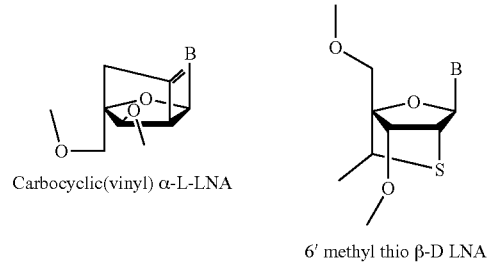

Carbocyclic(vinyl) α-L-LNA     6' methyl thio β-D LNA

As illustrated in the examples, in some embodiments of the invention the LNA nucleosides in the oligonucleotides are or comprise beta-D-oxy-LNA nucleosides.

Gapmer

The term gapmer as used herein refers to an antisense oligonucleotide which comprises a region of RNase H recruiting oligonucleotides (gap) which is flanked 5' and 3' by one or more affinity enhancing modified nucleosides (flanks). Various gapmer designs are described herein. Headmers and tailmers are oligonucleotides capable of recruiting RNase H where one of the flanks are missing, i.e. only one of the ends of the oligonucleotide comprises affinity enhancing modified nucleosides. For headmers the 3' flank is missing (i.e. the 5' flanc comprise affinity enhancing modified nucleosides) and for tailmers the 5' flank is missing (i.e. the 3' flank comprises affinity enhancing modified nucleosides).

LNA Gapmer

The term LNA gapmer is a gapmer oligonucleotide wherein at least one of the affinity enhancing modified nucleosides is an LNA nucleoside.

Mixed Wing Gapmer

The term mixed wing gapmer refers to a LNA gapmer wherein the flank regions comprise at least one LNA nucleoside and at least one non-LNA modified nucleoside, such as at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-DNA, arabino nucleic acid (ANA), 2'-fluoro-ANA and 2'-F-ANA nucleoside(s). In some embodiments the mixed wing gapmer has one flank which comprises LNA nucleosides (e.g. 5' or 3') and the other flank (3' or 5' respectfully) comprises 2' substituted modified nucleoside(s).

Length

When referring to the length of a nucleotide molecule as referred to herein, the length corresponds to the number of monomer units, i.e. nucleotides, irrespective as to whether those monomer units are nucleotides or nucleotide analogues. With respect to nucleotides, the terms monomer and unit are used interchangeably herein.

The process of the present invention is particularly suitable for the purification of short oligonucleotides, for example, consisting of 7 to 30 nucleotides, such as 7-10, such as 7, 8, 9, 10 or 10 to 20 nucleotides, such as 12 to 18 nucleotides, for example, 12, 13, 14, 15, 16, 17 or 18 nucleotides.

EXAMPLES

Example 1

Synthesis of isobutyryl protected LNA-G phosporamidite is described in Koshkin et al, Tetrahedron (1998), 54(14), 3607-3630.

Crude phosphorothioate oligonucleotides were synthesized in DMT-OFF mode at 20 μmol scale on a NittoPhase UnyLinker 200 polystyrene support by standard phosphoramidite chemistry, except for oligonucleotides in entry 17-18 which were synthesized on a 3'-Amino-Modifier C7 CPG support, 4,5-dicyanoimidazole was used as activator and xanthane hydride was used for thiooxidation. Standard DNA phosphoramidites with benzoyl protected A and C were used. LNA phosphoramidites with benzoyl protected A and 5-methyl-C were used. LNA-G was DMF- or iBu-protected as indicated in the table below.

5'-TFA-Amino-Modifier C6-CE phosphoramidite, available from Link Technologies, Lanakshire, Scotland, was used to introduce the 6-aminohexyl linker (AM-C6) in the 5'-end.

Amino-Modifier C6-dT-CE Phosphoramidite (5'-Dimethoxytrityl-5-[N-(tifluoroacetylaminohexyl)-3-acrylimido]-2'-deoxyUridine,3'-[(2-cyanoethyl)-(N,N-diisopropyl)]-phosphoramidite), available from Glen Research, Sterling, Va., was used to introduce the 5-[N-(aminohexyl)-3-acrylimido]-2'-deoxyuridine linker ($t^{AMC6}$).

11-(trifluoroacetamido)-3,6,9-trioxaundecan-1-yl-[(2-cyanoethyl)-(N,N-diisopropyl)]-phosphoramidite, available from Link Technologies. Lanakshire, Scotland, was used to introduce the 11-amino-3,6,9-trioxaundecan-1-yl group in the 5'-end (AM-TEG).

3'-Amino-Modifier C7 CPG (2-Dimethoxytrityloxymethyl-6-fluorenylmethoxycarbonylamino-hexane-1-succinoyl)-long chain alkylamino-CPG), available from Glen Research, Sterling, Va., was used to introduce the 6-amino-2-(hydroxymethyl)-hexyl group (AM-C7) in the 3'-end. In this case, after end of synthesis the support was treated with first a solution of diethylamine and then with 20% piperidine in DMF to remove the Fmoc group.

After end synthesis, the support was washed with a solution of diethylamine and then suspended in 1 mL concentrated ammonium hydroxide at 60° C. over night. The support was filtered off and the solution was evaporated to dryness under vacuum. The crude material was analyzed by UPLC-MS and ratios of +28 Da impurity compared to correct product was estimated by peak area at 260 nm.

| Entry (SEQ ID NO) | Sequence | LNA-G | Amount of +28 Da impurity |
|---|---|---|---|
| 1 | 5'-AM-C6-TGctatttcatctTGG-3' | DMF | 10.0% |
| 2 | 5'-AM-C6-TTctatttcatctTCT-3' | | 0.0% |
| 3 | 5'-AM-C6-AtGcTcGaTG-3' | DMF | 9.3% |
| 4 | 5'-AM-C6-AtGcTcGaTG-3' | iBu | 0.0% |
| 5 | 5'-AM-C6-GCTGATGAGT-3' | DMF | 7.5% |
| 6 | 5'-AM-C6-GCTGATGAGT-3' | iBu | 0.0% |
| 7 | 5'-AM-C6-CGGtaacttcaGCA-3' | DMF | 15.3% |
| 8 | 5'-AM-C6-CGGtaacttcaGCA-3' | iBu | 0.0% |
| 9 | 5'-AM-C6-atGTtcGGcaTGtG-3' | DMF | 17.7% |
| 10 | 5'-AM-C6-atGTtcGGcaTGtG-3' | iBu | 0.0% |
| 11 | 5'-AM-C6-GGatGGtcGTaaGG-3' | DMF | 21.7% |
| 12 | 5'-AM-C6-GGatGGtcGTaaGG-3' | iBu | 0.0% |
| 13 | 5'-atGTt$^{AMC6}$cGGcaTGtG-3' | DMF | 25.0% |
| 14 | 5'-atGTt$^{AMC6}$cGGcaTGtG-3' | iBu | 0.0% |
| 15 | 5'-AM-TEG-GGatGGtcGTaaGG-3' | DMF | 19.6% |
| 16 | 5'-AM-TEG-GGatGGtcGTaaGG-3' | iBu | 0.0% |
| 17 | 5'-GGatGGtcGTaaGG-AM-C7-3' | DMF | 13.4% |
| 18 | 5'-GGatGGtcGTaaGG-AM-C7-3' | iBu | 0.0% |

Upper case = LNA, lower case = DNA. AM-C6 = 6-aminohexyl, $t^{AMC6}$ = 5-[N-(aminohexyl)-3-acrylimido]-2'-deoxyuridine, AM-TEG = 11-amino-3,6,9-trioxaundecan-1-yl, AM-C7 = 6-amino-2-(hydroxymethyl)-hexyl. The examples were fully phosphorothioate oligonucleotides, where the LNA monomers were beta-D-oxy LNA. The LNA-C monomers are 5-methyl cytosine LNA monomers.

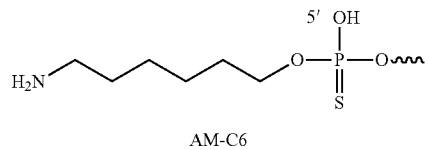

AM-C6

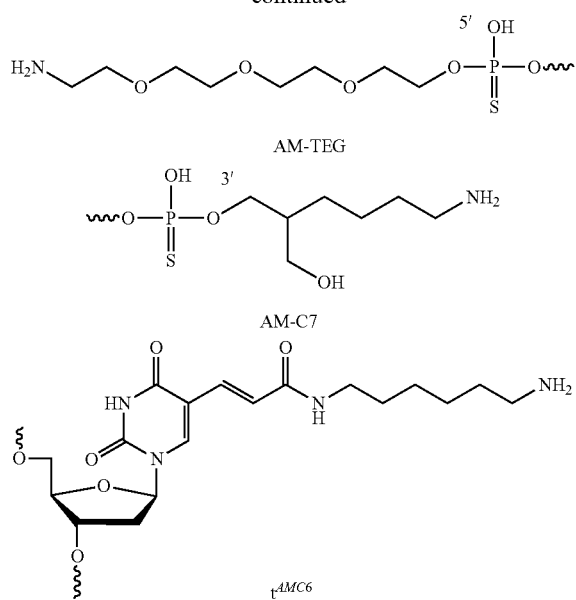

Example 2

A 5'-aminohexyl linked phosphorothioate oligonucleotide with sequence 5'-AM-C6-caGCGtaaagagAGG-3' was prepared using DMF-protected LNA-G and iBu-protected DNA-G phosphoramidites as described in example 1. The crude material contained the full length product (FL) and approximately 20% of the formyl (HCO,+28) impurity (FL+28)

By analysis with an ultra-high resolution mass spectrometer (FT-ICR-MS type; Thermo LTQ-FT Ultra) we determined the exact mass difference of the two $[M-5H]^{5'}$ peaks to 27.9968 Da (for FL 1044.11945 Da, for FL+28 1049.71881 Da) (FIG. 1) The mass difference of 5.59936 Da for the 5-times charged ions results in 5.59936 Da*5=27.9968 Da for the uncharged molecule (FIG. 3).

The measured mass is within Δ=1.885 mmu accuracy to a carbonyl group (CO) and the potential next modification with a nominal mass of +28 Da is "N2" where the exact mass difference is −9.348 mmu which is already outside of the mass accuracy of the instrument used.

For determination of the exact position of the CO-modification a mass spectrometric sequencing of the molecule was done by MS/MS with the same instrument. For nomenclature of oligonucleotide fragmentation see McLuckey et al., J. Am. Chem. Soc., 115, 25, 12085-12095.

In the MS/MS experiment both 5-time charged ions (w/ and w/o modification) were fragmented. Here we located the modification on ions from the 5'-end up to the eighth nucleotide whereas the nucleotides from the 3'-end broke up at the same position with no modification. No further 3'-fragments with longer sequences were detectable. In the resulting spectra the b4-ion (FIG. 4) was observed for FL and also for FL+28.

A further fragmentation with MS3 of the b4-ion (FIG. 4) resulted in spectra which show amongst other signals the a2-B ion and the b4-Cytosine ion at the first nucleotide (b4-C). This two ions lead to the proposal that the modification is located on the C6-aminolinker (FIG. 5).

Since only the amino linker group is present in both structures as possible reaction partner for modification we conclude that a formyl amide is formed at that position (FIG. 6).

---

The invention claimed is:

1. A method of preparing a LNA oligonucleotide comprising the steps of:
   a) incorporating at least one LNA-G monomer comprising an acyl protected exocyclic nitrogen into an oligonucleotide, wherein the acyl protection group on the exocyclic nitrogen of the LNA-G monomer(s) is isobutyryl (iBu);
   b) incorporating at least one optionally protected aliphatic amine group into the oligonucleotide; and,
   c) deprotecting the acyl protected exocyclic nitrogen of the at least one LNA-G monomer by removal of the acyl protection group,
   wherein steps a) and b) can occur in either order.

2. The method according to claim 1 wherein the optionally protected aliphatic amine group is a primary or secondary amine.

3. The method according to claim 1, wherein the optionally protected aliphatic amine group is a non nucleosidic amine group.

4. The method according to claim 1, wherein the optionally aliphatic amine group is selected from the group consisting of an amino alkyl, alkylamino alkyl, piperidine, piperazine, pyrrolidine and imidazole.

5. The method according to claim 1, wherein the optionally aliphatic amine group is selected from the group consisting of 5'-TFA-Amino-Modifier-C5-CE Phosphoramidite, 5'-TFA-Amino-Modifier C6-CE Phosphoramidite, 11-(trifluoroacetamido)-3,6,9-trioxaundecan-1-yl-[(2-cyanoethyl)-(N,N-diisopropyl)]-phosphoramidite, 5-TFA-Amino-Modifier-C12-CE Phosphoramidite, Amino-Modifier C2-dT-CE Phosphoramidite, Amino-Modifier C6-dA-CE Phosphoramidite, Amino-Modifier C6-dA-CE Phosphoramidite, Amino-Modifier C6-dT-CE Phosphoramidite, N2-Amino-Modifier C6 dG, Fmoc Amino-Modifier C6 dT, 3'-Amino-Modifier C7 CPG 1000, 3'-Amino-Modifier C6-dC CPG, 3'-Amino-Modifier C6-dC CPG, 3'-PT-Amino-Modifier C6 CPG, 3'-Amino-Modifier C6-dT CPG, PC 5'-Amino-Modifier-CE Phosphoramidite, 5'-Amino-Modifier C6-PDA, 5'-Amino-Modifier C12-PDA, 5'-Amino-Modifier TEG PDA, Amino-Modifier Serinol and 3'-Amino-Modifier Serinol CPG.

6. The method according to claim 1, wherein the optionally protected aliphatic amine group is an amino hexyl linker.

7. The method according to claim 1, wherein the aliphatic amine group is incorporated into the oligonucleotide via the incorporation of an amino-modified monomer.

8. The method according to claim 7, wherein the aliphatic amino-modified monomer is a phosphoramidite, a H phosphonate or a phosphotriester monomer.

9. The method according to claim 7, wherein the amino-modified monomer is a phosphoramidite.

10. The method according to claim 1, wherein, if present, other G residues incorporated into the oligonucleotide also comprise an acyl protection group.

11. The method according to claim 1, wherein the LNA-G monomer(s), and optionally when present other G monomers, is a phosphoramidite, a H-phosphonate or a phosphotriester monomer.

12. The method according to claim 1, wherein the LNA-G monomer(s), and optionally when present other G monomers, is a phosphoramidite.

13. The method according to claim 1, wherein the LNA-G monomer comprises a 2'-O—CH$_2$-4' biradical in the furanose ring.

14. The method according to claim 1, wherein step c) further comprises deprotection of the aliphatic amine group.

15. The method according to claim 1, wherein step c) comprises deprotection of the oligonucleotide performed in the presence of ammonia.

16. The method according to claim 1, wherein step c) is followed by an additional step (d) which comprises incorporating a conjugate group onto the aliphatic primary amine group.

17. The method according to claim 16, wherein the conjugate group is a non-nucleotide moiety, selected from the group consisting of a lipid, a sterol, a carbohydrate, a peptide and a protein.

18. The method according to claim 1, wherein at least steps a)-c) are performed on a solid support and are followed by the cleavage of the oligonucleotide from the solid support which may be performed during step c) or subsequent to step c).

19. The method according to claim 1, wherein the acyl protection group(s) is isobutyryl and the aliphatic primary amine group(s) is an aminohexyl linker.

20. The method of claim 15 wherein the deprotection of the oligonucleotide is performed in a solution of ammonium hydroxide.

21. An LNA oligonucleotide which comprises at least one LNA-G monomer comprising an acyl protected exocyclic nitrogen and at least one optionally protected aliphatic amine group, wherein said LNA oligonucleotide is attached to a solid support, and wherein the acyl protection group on the acyl protected exocyclic nitrogen of the LNA-G monomer(s) is isobutyryl (iBu).

* * * * *

SEQUENCE LISTING

<160> NUMBER OF SEQ ID NOS: 18

<210> SEQ ID NO 1
<211> LENGTH: 16
<212> TYPE: DNA
<213> ORGANISM: Artificial
<220> FEATURE:
<223> OTHER INFORMATION: Oligonucleotide base sequence

<400> SEQUENCE: 1
tgctatttca tcttgg                                                   16

<210> SEQ ID NO 2
<211> LENGTH: 16
<212> TYPE: DNA
<213> ORGANISM: Artificial
<220> FEATURE:
<223> OTHER INFORMATION: Oligonucleotide base sequence

<400> SEQUENCE: 2
ttctatttca tcttct                                                   16

<210> SEQ ID NO 3
<211> LENGTH: 10
<212> TYPE: DNA
<213> ORGANISM: Artificial
<220> FEATURE:
<223> OTHER INFORMATION: Oligonucleotide base sequence

```
<400> SEQUENCE: 3
atgctcgatg                                                              10

<210> SEQ ID NO 4
<211> LENGTH: 10
<212> TYPE: DNA
<213> ORGANISM: Artificial
<220> FEATURE:
<223> OTHER INFORMATION: Oligonucleotide base sequence

<400> SEQUENCE: 4
atgctcgatg                                                              10

<210> SEQ ID NO 5
<211> LENGTH: 10
<212> TYPE: DNA
<213> ORGANISM: Artificial
<220> FEATURE:
<223> OTHER INFORMATION: Oligonucleotide base sequence

<400> SEQUENCE: 5
gctgatgagt                                                              10

<210> SEQ ID NO 6
<211> LENGTH: 10
<212> TYPE: DNA
<213> ORGANISM: Artificial
<220> FEATURE:
<223> OTHER INFORMATION: Oligonucleotide base sequence

<400> SEQUENCE: 6
gctgatgagt                                                              10

<210> SEQ ID NO 7
<211> LENGTH: 14
<212> TYPE: DNA
<213> ORGANISM: Artificial
<220> FEATURE:
<223> OTHER INFORMATION: Oligonucleotide base sequence

<400> SEQUENCE: 7
cggtaacttc agca                                                         14

<210> SEQ ID NO 8
<211> LENGTH: 14
<212> TYPE: DNA
<213> ORGANISM: Artificial
<220> FEATURE:
<223> OTHER INFORMATION: Oligonucleotide base sequence

<400> SEQUENCE: 8
cggtaacttc agca                                                         14

<210> SEQ ID NO 9
<211> LENGTH: 14
<212> TYPE: DNA
<213> ORGANISM: Artificial
<220> FEATURE:
<223> OTHER INFORMATION: Oligonucleotide base sequence

<400> SEQUENCE: 9
atgttcggca tgtg                                                         14

<210> SEQ ID NO 10
```

```
<211> LENGTH: 14
<212> TYPE: DNA
<213> ORGANISM: Artificial
<220> FEATURE:
<223> OTHER INFORMATION: Oligonucleotide base sequence

<400> SEQUENCE: 10
atgttcggca tgtg                                                         14

<210> SEQ ID NO 11
<211> LENGTH: 14
<212> TYPE: DNA
<213> ORGANISM: Artificial
<220> FEATURE:
<223> OTHER INFORMATION: Oligonucleotide base sequence

<400> SEQUENCE: 11
ggatggtcgt aagg                                                         14

<210> SEQ ID NO 12
<211> LENGTH: 14
<212> TYPE: DNA
<213> ORGANISM: Artificial
<220> FEATURE:
<223> OTHER INFORMATION: Oligonucleotide base sequence

<400> SEQUENCE: 12
ggatggtcgt aagg                                                         14

<210> SEQ ID NO 13
<211> LENGTH: 14
<212> TYPE: DNA
<213> ORGANISM: Artificial
<220> FEATURE:
<223> OTHER INFORMATION: Oligonucleotide base sequence

<400> SEQUENCE: 13
atgttcggca tgtg                                                         14

<210> SEQ ID NO 14
<211> LENGTH: 14
<212> TYPE: DNA
<213> ORGANISM: Artificial
<220> FEATURE:
<223> OTHER INFORMATION: Oligonucleotide base sequence

<400> SEQUENCE: 14
atgttcggca tgtg                                                         14

<210> SEQ ID NO 15
<211> LENGTH: 14
<212> TYPE: DNA
<213> ORGANISM: Artificial
<220> FEATURE:
<223> OTHER INFORMATION: Oligonucleotide base sequence

<400> SEQUENCE: 15
ggatggtcgt aagg                                                         14

<210> SEQ ID NO 16
<211> LENGTH: 14
<212> TYPE: DNA
<213> ORGANISM: Artificial
<220> FEATURE:
<223> OTHER INFORMATION: Oligonucleotide base sequence
```

```
<400> SEQUENCE: 16
ggatggtcgt aagg                                                        14

<210> SEQ ID NO 17
<211> LENGTH: 14
<212> TYPE: DNA
<213> ORGANISM: Artificial
<220> FEATURE:
<223> OTHER INFORMATION: Oligonucleotide base sequence

<400> SEQUENCE: 17
ggatggtcgt aagg                                                        14

<210> SEQ ID NO 18
<211> LENGTH: 14
<212> TYPE: DNA
<213> ORGANISM: Artificial
<220> FEATURE:
<223> OTHER INFORMATION: Oligonucleotide base sequence

<400> SEQUENCE: 18
ggatggtcgt aagg                                                        14
```